(12) United States Patent
Bunch (10) Patent No.: US 8,945,060 B2
(45) Date of Patent: Feb. 3, 2015

(54) ACCESS SHEATH AND NEEDLE ASSEMBLY FOR DELIVERING THERAPEUTIC MATERIAL

(75) Inventor: Tyler Joseph Bunch, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 320 days.

(21) Appl. No.: 13/376,010

(22) PCT Filed: Jun. 4, 2010

(86) PCT No.: PCT/US2010/037430
§ 371 (c)(1),
(2), (4) Date: Dec. 2, 2011

(87) PCT Pub. No.: WO2010/141837
PCT Pub. Date: Dec. 9, 2010

(65) Prior Publication Data
US 2012/0071832 A1    Mar. 22, 2012

Related U.S. Application Data

(60) Provisional application No. 61/184,474, filed on Jun. 5, 2009.

(51) Int. Cl.
*A61M 5/178* (2006.01)
*A61M 25/00* (2006.01)
*A61M 25/01* (2006.01)

(52) U.S. Cl.
CPC ......... *A61M 25/0084* (2013.01); *A61M 25/007* (2013.01); *A61M 25/0136* (2013.01); *A61M 25/0147* (2013.01); *A61M 2025/0087* (2013.01)
USPC ...... 604/173; 604/164.01; 604/525; 604/526; 604/528

(58) Field of Classification Search
CPC ................... A61M 25/0012; A61M 25/0015; A61M 25/0026; A61M 25/0043; A61M 25/0045; A61M 25/005; A61M 25/0053; A61M 25/0054; A61M 25/007; A61M 25/0084; A61M 15/0141; A61M 25/0144; A61M 25/0147; A61M 25/06; A61M 25/0606
USPC .............. 604/93.01, 173, 264, 272, 523, 524, 604/525, 526, 528, 158, 164.01
See application file for complete search history.

(56) References Cited

U.S. PATENT DOCUMENTS 4,578,061 A    3/1986 Lemelson
5,312,376 A *  5/1994 Van Heugten ........... 604/168.01
(Continued)

FOREIGN PATENT DOCUMENTS

WO    WO 92/10142    6/1992

OTHER PUBLICATIONS

Equivalent Diameter, The Engineering Toolbox, Feb. 23, 2009.*

*Primary Examiner* — Bhisma Mehta
*Assistant Examiner* — Nicholas Meghri
(74) *Attorney, Agent, or Firm* — Brinks Gilson & Lione (57) ABSTRACT

Medical device (10) for delivering therapeutic material to a patient. The device comprises an access sheath (12) having a proximal section (18) extending to a distal section (20). A working lumen (22) is formed in the proximal and distal sections. The distal section has a plurality of side ports (48) formed therethrough in fluid communication with the working lumen. The distal section has a deflection section (42) actuatable to bend at an angle for positioning the side ports in the patient. A needle assembly (14) is configured to move within the working lumen between a retracted position and an extended position. In fluid communication with a central lumen is a plurality of needles (80). The needles are disposed within the access sheath in the retracted position and the needles extend through the side ports outwardly from the access sheath in the extended position.

17 Claims, 8 Drawing Sheets

(56) References Cited

U.S. PATENT DOCUMENTS

| | | | |
|---|---|---|---|
| 5,354,279 A * | 10/1994 | Hofling | 604/173 |
| 5,360,416 A | 11/1994 | Ausherman et al. | |
| 5,419,777 A | 5/1995 | Hofling | |
| 5,720,719 A | 2/1998 | Edwards et al. | |
| 5,792,110 A | 8/1998 | Cunningham | |
| 6,302,870 B1 | 10/2001 | Jacobsen et al. | |
| 6,425,887 B1 | 7/2002 | McGuckin et al. | |
| 6,447,477 B2 | 9/2002 | Burney et al. | |
| 6,551,278 B1 * | 4/2003 | Geitz | 604/131 |
| 6,969,371 B2 | 11/2005 | Palasis et al. | |
| 6,989,004 B2 | 1/2006 | Hinchliffe et al. | |
| 7,331,947 B2 | 2/2008 | McGuckin, Jr. et al. | |
| 2002/0049414 A1 * | 4/2002 | Nobles et al. | 604/173 |
| 2003/0195470 A1 | 10/2003 | Ponzi | |
| 2004/0064098 A1 * | 4/2004 | Cuschieri et al. | 604/158 |
| 2004/0068242 A1 | 4/2004 | McGuckin, Jr. | |
| 2005/0070844 A1 * | 3/2005 | Chow et al. | 604/95.04 |
| 2005/0096629 A1 | 5/2005 | Gerber et al. | |
| 2006/0041243 A1 | 2/2006 | Nayak et al. | |
| 2006/0129101 A1 * | 6/2006 | McGuckin, Jr. | 604/164.01 |
| 2006/0189940 A1 | 8/2006 | Kirsch | |
| 2007/0135768 A1 | 6/2007 | Carlsen | |
| 2007/0179455 A1 * | 8/2007 | Geliebter et al. | 604/272 |
| 2007/0203474 A1 * | 8/2007 | Ryan et al. | 604/528 |

* cited by examiner

ACCESS SHEATH AND NEEDLE ASSEMBLY FOR DELIVERING THERAPEUTIC MATERIAL

CROSS REFERENCE TO RELATED APPLICATIONS

This application is related to and claims the benefit of priority to PCT/US2010/037430, filed on Jun. 4, 2010 which application claims priority to and all available benefits of U.S. Provisional Patent Application No. 61/184,474, filed Jun. 5, 2009, entitled "ACCESS SHEATH AND NEEDLE ASSEMBLY FOR DELIVERING THERAPEUTIC MATERIAL," both of which are hereby incorporated by reference in their entirety.

BACKGROUND OF THE INVENTION

1. Field of the Invention

The present invention relates to medical devices. More particularly, the present invention relates to a medical injection device and a method for delivering therapeutic material to a patient.

2. Background of the Invention

Arteries carry blood rich in oxygen and nutrients from the heart to the rest of the body. As we age, a fatty material called plaque can build up in the walls of the arteries, causing them to narrow or become blocked, which can reduce or block blood flow. This condition may result in various diseases, such as for example, Peripheral Artery Disease (PAD) and Peripheral Vascular Disease (PVD), which can adversely affect blood flow to and throughout the legs.

Early symptoms of PAD include pain, cramping, or weakness in the legs from walking or climbing stairs, which may be relieved after resting. Often, as plaque continues to build up on the walls of the arteries in the legs, the symptoms of PAD can become frequent and severe. In the advanced stage of PAD, blood flow to one or both legs can become severely limited. Severely blocked arteries in the leg and sharply diminished blood flow can result in wounds that do not heal, pain in the feet or legs, infections, and even gangrene. This painful condition is known as Critical Limb Ischemia (CLI), which may result in amputation of the leg.

Medical treatments including angioplasty, stents, and bypass surgery may be implemented to repair blocked circulation in patients' legs with CLI. More recently, other forms of treatment are being included with the surgical treatments and/or as independent treatments. For example, wounds may result from the surgical procedures for improving blood flow. If the wounds do not proceed normally to heal or if the amount of tissue destruction is large, advanced cell based technologies and bio-active wound adjuncts which deliver exogenous growth factors to the wound bed and offer immediate tissue coverage may be used. Examples of living tissue equivalents include APLIGRAF® and DERMAGRAFT®. APLIGRAF® consists of living human dermal fibroblasts and keratinocytes in a bovine collagen matrix. DERMAGRAFT® is a living human fibroblast dermal substitute. Examples of bio-activated wound adjuncts include GRAFT JACKET® matrix which is a human allograft product, INTEGRA®, a bovine collagen and chondroitin-6-sulfate, OASIS®, and a cellular product consisting of porcine intestinal submucosa, and other extracellular matrix (ECM), such as small intestinal submucosa (SIS). Further treatments for PAD currently in development include stem cell therapy as well. Many of these therapeutic materials are relatively viscous materials making the process of injecting them into the vessels of the vasculature difficult to perform. For example, conventional needles may have marginally sufficient or even insufficient flow capacity for delivering relatively viscous therapeutic materials to a desired treatment site. Moreover, the body passageway used for advancing the needle to the desired treatment site may be tortuous.

In view of the above, it may be desirable to have an improved medical injection device for delivering therapeutic materials and treatments into the vasculature of a patient.

BRIEF SUMMARY OF THE INVENTION

In at least one embodiment of the present invention, a medical device for delivering therapeutic material to a patient is provided. The device comprises an access sheath having a proximal section extending to a distal section. A working lumen is formed in the proximal and distal sections. The distal section has a plurality of side ports formed therethrough in fluid communication with the working lumen. The distal section has a deflection section actuatable to bend at an angle for positioning the side ports in the patient. A needle assembly is configured to move within the working lumen between a retracted position and an extended position. The needle assembly includes a main cannula having a proximal portion extending to a distal portion. A central lumen is formed in the proximal and distal portions, and is configured to advance the therapeutic material. In fluid communication with the central lumen is a plurality of needles. The needles are attached to the distal portion of the main cannula and extend distally therefrom such that the needles are disposed within the access sheath in the retracted position and the needles extend through the side ports outwardly from the access sheath in the extended position to deliver the therapeutic material to the patient.

In at least one other embodiment of the present invention, a medical system for delivering therapeutic material to a patient is provided. The system comprises an access sheath and a needle assembly as discussed in the foregoing paragraph. A control handle for actuation by an interventionalist is provided. The access sheath is operably connected to the control handle such that the deflection section bends at an angle in response to actuation of the control handle.

An example of a method for delivering therapeutic material to a patient in accordance with the present invention is provided. The method comprises actuating a deflection section of an access sheath to bend at an angle to position a plurality of side ports formed through a distal section of the access sheath. A needle assembly is moved within a working lumen of the access sheath to an extended position to extend a plurality of needles of the needle assembly through the side ports outwardly from the access sheath. Therapeutic material is advanced through a central lumen of a main cannula of the needle assembly. The needles are in fluid communication with the central lumen to deliver the therapeutic material to the patient.

Further objects, features, and advantages of the present invention will become apparent from consideration of the following description and the appended claims taken in conjunction with the accompanied drawings.

DETAILED DESCRIPTION OF THE INVENTION

Detailed embodiments of the present invention are disclosed herein. It is understood, however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting, but merely as a representative basis for the claims and for teaching one skilled in the art to practice the present invention.

Examples of the present invention seek to overcome some of the concerns associated with delivering therapeutic material to a patient via a needle where the therapeutic material may be relatively viscous and/or the body passageway for advancing the needle to a desired treatment site is tortuous.

Applying the principles of the present invention is a system comprising an access sheath that is deployable in the vasculature of a patient and a needle assembly that is configured to be advanced through the access sheath. The access sheath has side ports formed through its distal end portion and an active deflection section that is configured to bend to position and reposition the side ports to facilitate navigating along a body passageway which may be tortuous. The needle assembly has a relatively large main cannula which is preferably unobstructed to provide a relatively large flow area for advancing therapeutic material along its length to a plurality of relatively short and smaller needles arranged at the distal end of the main cannula. The main cannula is moveable within the access sheath to advance the needles through the side ports for delivering the therapeutic material to the desired treatment site. It is believed that the main cannula with a relatively large flow area reduces resistance for advancing even relatively viscous therapeutic material along the length of the cannula to the distally arranged needles, thereby enhancing the volumetric flow rate of the therapeutic material to the desired treatment site.

Figure 1A:
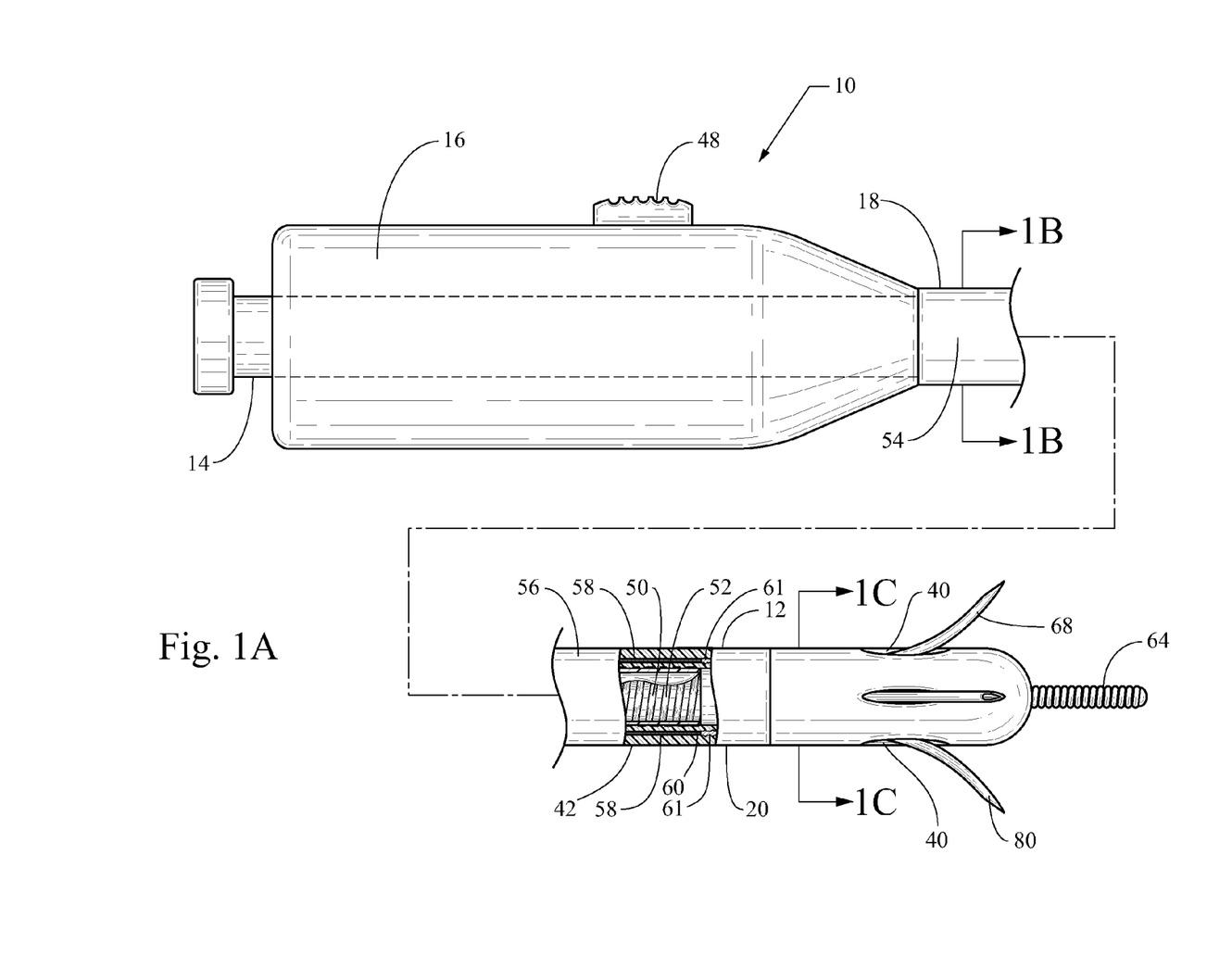
FIG. 1A is a tear-away side view of a medical system in accordance with an embodiment of the present invention.
Figure 1B:
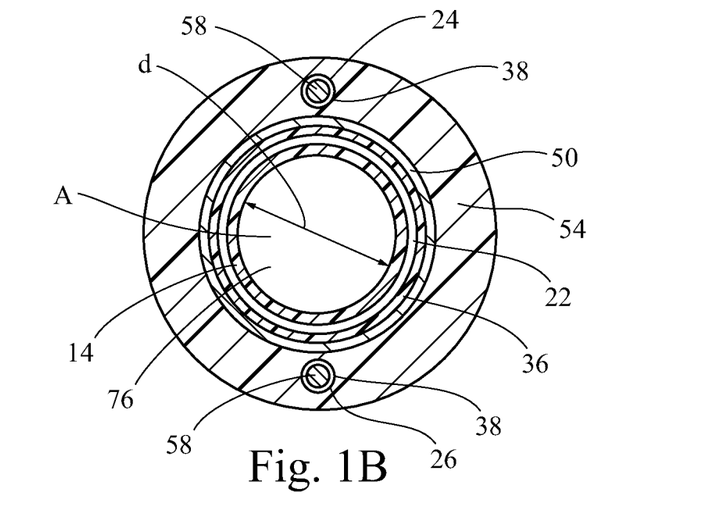
FIG. 1B is a cross-section of the medical system depicted in FIG. 1A.
Figure 1C:
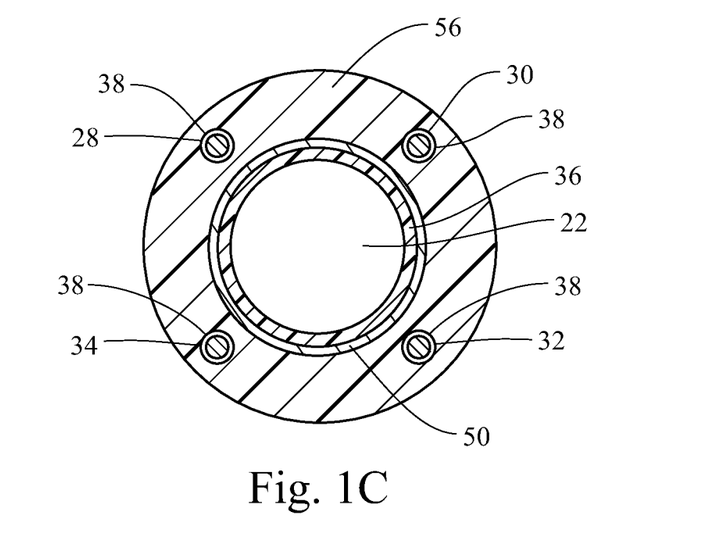
FIG. 1C is another cross-section of the medical system depicted in FIG. 1A.

Referring to FIGS. 1A-1C, at least one embodiment of a medical system for delivering therapeutic material to a patient is provided. The medical system 10 includes an access sheath 12, a needle assembly 14 and a control handle 16. The access sheath 12 is in the form of an elongated member and has a proximal section 18 and a distal section 20.

Several lumens are formed in the access sheath 12 and include a large or working lumen 22 and a plurality of smaller additional lumens 24, 26, 28, 30, 32 and 34. The working lumen 22 is lined with a layer of lubricious polymer 36, such as a fluoropolymer liner, e.g., polytetrafluoroethylene (PTFE) or TEFLON®. Preferably, the additional lumens 24, 26, 28, 30, 32 and 34 are also lined with a fluoropolymer liner 38 or other lubricious material on their inner surfaces. Polyethylene, polypropylene or other polymer may be used instead of a fluoropolymer.

In at least one embodiment, the access sheath 20 includes a coil wrapping 50 comprising a plurality of flat wire turns 52 which, for example, are positioned at an acute angle to the working lumen 22 and uniformly spaced apart in the range of about 0.005 inches to 0.015 inches between the turns 52. The coil wrapping 50 may be formed, for example, from 0.003 inch thick by 0.012 inch wide flat stainless steel wire. The coil wrapping 50 is compression fitted around the outer surface of the inner liner 36 of the working lumen 22.

Forming an exterior layer of the proximal section 18 and at least part of the distal section 20 (e.g. the deflection section 42 discussed further below) are polymer liners 54 and 56, respectively. The liners 54 and 56 are disposed about the coil wrapping 50. The polymer liner 54 of the proximal section 18 is made of a first polymer material and the liner 56 of at least the deflection section 42 of the distal section 20 is made of a second polymeric material. The first and second polymeric materials may be silicone, nylon or urethane. Other medically accepted thermoplastic or thermoset materials may also be used either separately or in combination, including PTFE, a fluoropolymer, polyethylene, polypropylene, acetyl, and others.

As illustrated, four of the additional lumens 28, 30, 32 and 34 are formed through the distal section 20 to define a plurality of side ports 40 (see FIG. 3 for a cross-sectional view of the side ports 40) that are in fluid communication with the working lumen 22. The four additional lumens 28, 30, 32 and 34 may be formed through the distal section 20 at radial intervals of 90 degrees. Alternatively, for example, the access sheath 12 may have three or two side ports 40 which may be arranged at radial intervals of 120 degrees and 180 degrees, respectively. Other suitable arrangements and radial intervals for positioning the additional lumens that form the side ports 40 may also be used.

Figure 3:
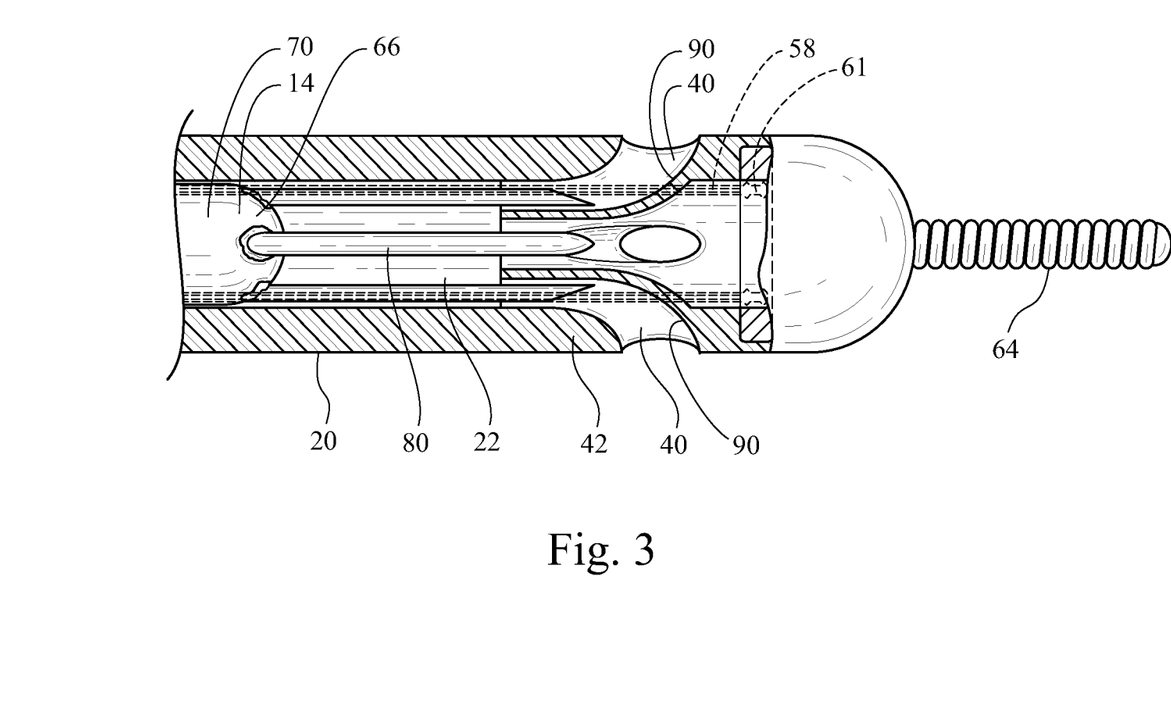
FIG. 3 is a partial cross-sectional view of the medical system in accordance with one embodiment of the present invention.

The distal section 20 has the deflection section 42 that is actuatable to bend at an angle (see FIG. 1D) for positioning and/or repositioning the side ports 40. As illustrated in FIG. 1A, the deflection section 42 may be spaced apart from and proximal to the side ports 40. Alternatively, the side ports 40 may be formed through the deflection section 42 as shown in FIG. 3. The deflection section 42 in one embodiment is actuatable to bend at an angle via actuation of a manual or thumb actuator 48 of the control handle 16 (discussed further below).

To facilitate bending of the deflection section 42, the second polymeric material of the distal liner 56 has a lower durometer than the first polymeric material of the proximal liner 54. In one example, the distal liner 56 has a Shore D durometer of between about 10 to 50 (preferably between about 25 and 40), and the proximal liner 54 has a Shore D durometer of between about 50 and 90 (preferably between 55 and 72).

In one embodiment, the access sheath 12 comprises at least one control wire 58 movably disposed in at least one of the additional lumens 24 and 26 for actively bending the deflection section 42. As illustrated, two control wires 58 are connected at their distal ends 60 to the distal section 20 of the access sheath 12 so that the deflection section 42 may be easily bent at an angle and maneuvered by an interventionalist. The two additional lumens 24 and 26 do not extend entirely through the distal section 20, but rather terminate within the distal section 20. The distal ends 60 of the control wires 58 are each anchored within the distal section 20 via an anchor 61 or cannula. The anchors 61 are disposed in the additional lumens 24 and 26 so that when tension is applied to at least one of the control wires 58, the tension is transferred from the control wire 58 through the anchor 61 to the deflection section 42, causing the deflection section 42 to bend at an angle to position the side ports 40.

Figure 4A:
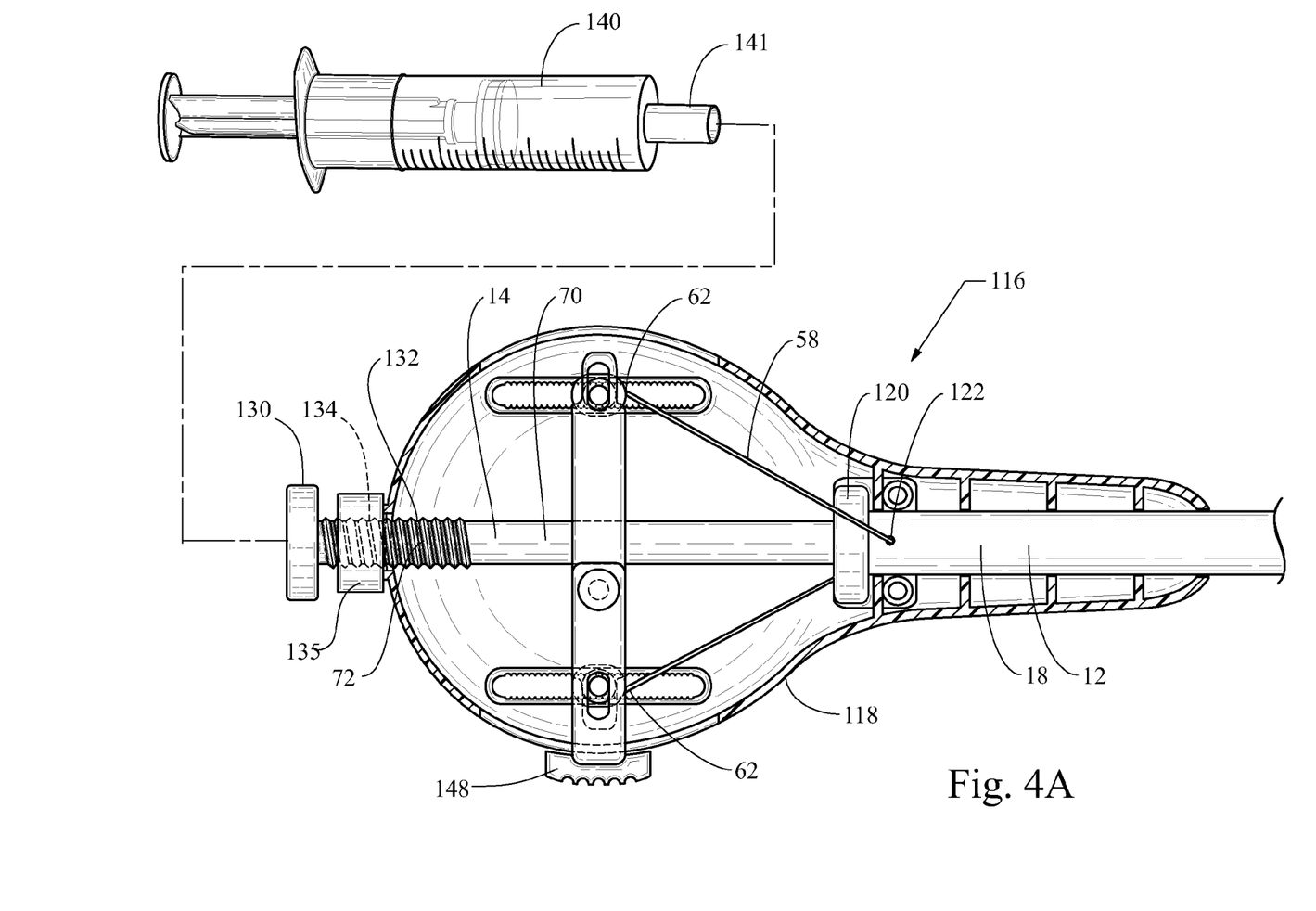
FIG. 4A is a partial cross-sectional side view of a medical system in accordance with an embodiment of the present invention.
Figure 4B:
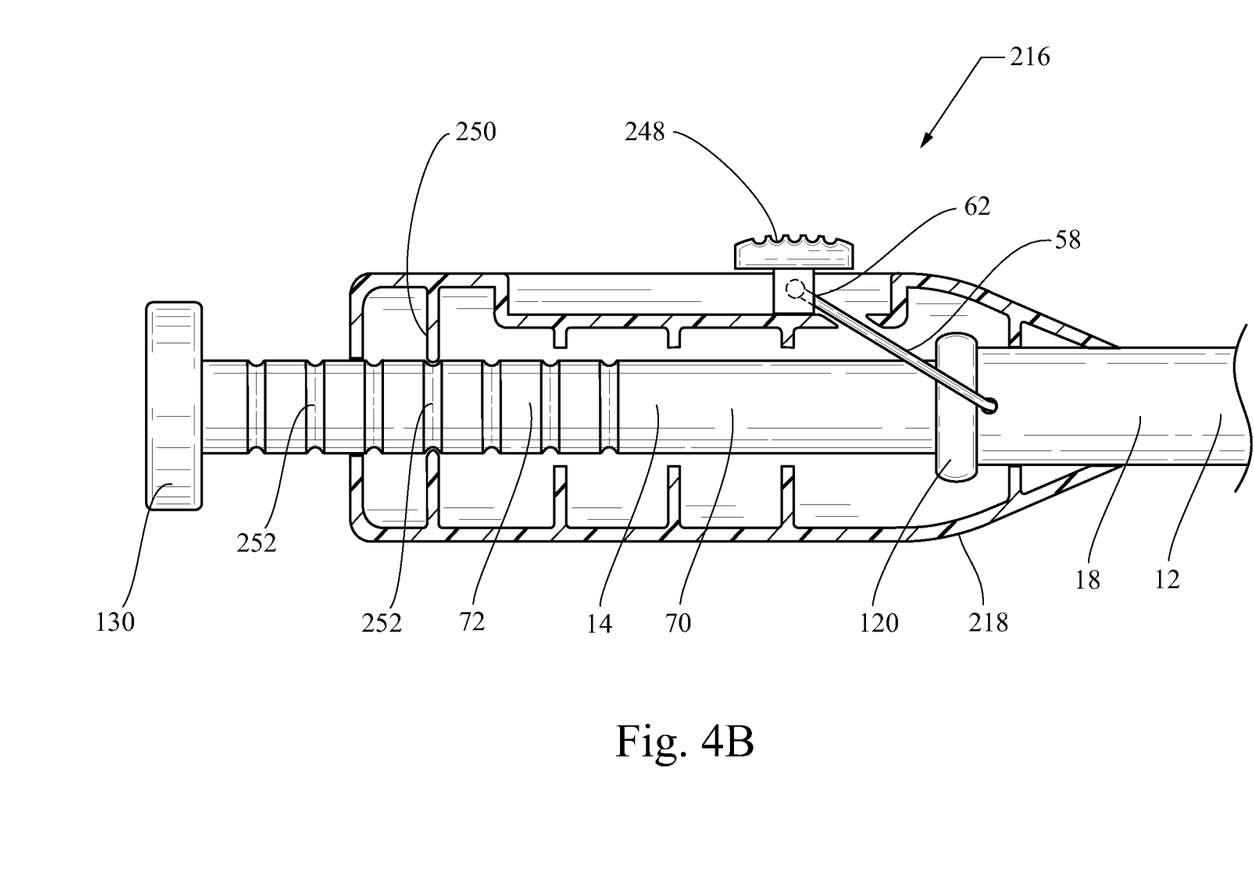
FIG. 4B is a partial cross-sectional side view of a medical system in accordance with another embodiment of the present invention.

The proximal ends 62 of the control wires 58 may be joined to the control handle 16, such as for example, to the thumb actuator 48 as shown in FIGS. 1A, 4A-4B, or otherwise, for manipulation of the control wires 58. The control wires 58 may each be made of a single steel wire, or may be a wire bundle. Alternatively, the control wires 58 may use filaments made from other materials, such as nylons, polyesters, or other polymers, or polymer reinforced with glass, carbon, or metallic wires or fibers.

Figure 1D:
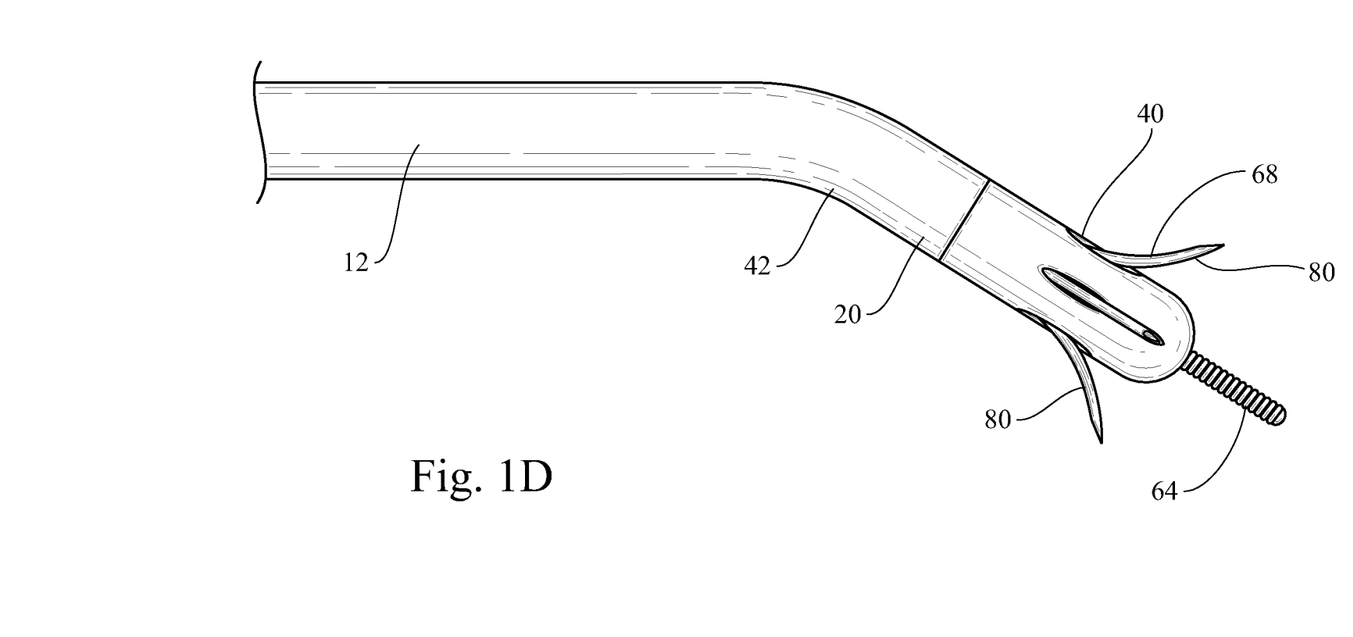
FIG. 1D is a partial side view of the medical system in accordance with one embodiment of the present invention.

As illustrated in FIGS. 1A and 1D, the access sheath 12 preferably includes an elongated guide tip 64 attached at the distal-most end of the distal section 20. The guide tip 64 is preferably sufficiently flexible to bend to facilitate navigating through a tortuous body passageway of a patient for guiding the access sheath 12 and yet, is sufficiently stiff to provide tactile feedback to allow the interventionalist to feel movement or bending of the elongated guide tip 64 as it is being advanced through the body passageway.

Figure 2A:
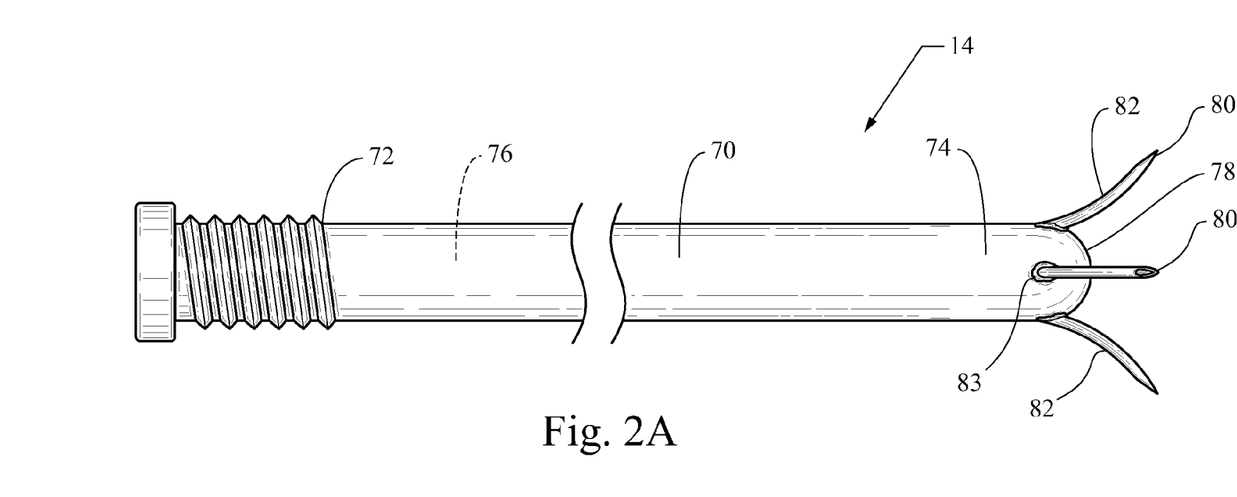
FIG. 2A is a side view of a needle assembly in accordance with one embodiment of the present invention.
Figure 2B:
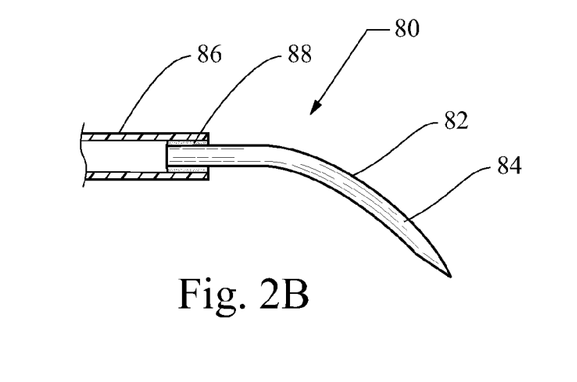
FIG. 2B is a side view of a needle in accordance with an embodiment of the present invention.

Referring also to FIGS. 2A-3, the needle assembly 14 comprises a main cannula 70 having a proximal portion 72 extending to a distal portion 74. A central lumen 76 is formed through the proximal portion 72 and terminates in the distal portion 74 at the distal-most wall 78. The central lumen 76 is for advancing therapeutic material from the proximal portion 72 to the distal portion 74. As illustrated in FIG. 1B, the central lumen 76 has a diameter (d) defining an unobstructed flow area (A) for advancing the therapeutic material, where $A=\pi(d/2)^2$.

As illustrated, a plurality of needles 80 are attached to the distal portion 74 of the main cannula 70 adjacent the distal-most wall 78. The needles 80 extend distally from the distal portion 74 and are in fluid communication with the central lumen 76. The needle assembly 14 is configured to be moved in the working lumen 22 between a retracted position 66 (see FIG. 3) and an extended position 68 (see FIGS. 1A and 1D). In the retracted position 66, the needles 80 are disposed within the access sheath 12. When the main cannula 70 is moved within the working lumen 22 to the extended position 68, the needles 80 extend through the side ports 40 outwardly from the access sheath 12 for delivering the therapeutic material to the patient.

In at least one embodiment, each of the needles 80 have a curved portion 82 which helps position the needle 80 outwardly from the access sheath 12 when the main cannula 70 is moved to the extended position 68. As illustrated in FIG. 2B, the needles 80 each have a distal metal section 84 and a proximal plastic section 86 that are joined together via an adhesive 88. Alternatively, the distal metal section 84 may be overmolded with plastic to fluidly connect and form the proximal plastic section 86. The needles 80 may be attached to the main cannula 70, such as for example, by soldering joints 83 or welding joints. Other suitable constructions for making and/or attaching the needles may also be used including for example, making the needles 80 from a super-elastic material such as Nitinol or a flexible polymer to facilitate bending and/or flexing of the needles 80.

As illustrated in FIG. 3, the additional lumens 28, 30, 32 and 34 of the side ports 40 are curved distally outward. Accordingly, when the main cannula 70 is moved to the extended portion 68, the needles 80 move along the curved portions 90 of the additional lumens 28, 30, 32 and 34 which help position at least the tip portions of the needles 80 outwardly from the access sheath 12.

Referring to FIG. 4A, at least one embodiment for the control handle 116 is provided. As illustrated, the control handle 116 has easy to use controls so that the interventionalist can readily adjust the position of the side ports 40 via the deflection section 42. A housing 118 is preferably molded about the proximal section 18 of the access sheath 12, or otherwise assembled in place. In particular, the access sheath 12 has a sheath hub 120 formed at the proximal end of the proximal section 18. The housing 118 is disposed about the sheath hub 120 to hold the proximal section 18 of the access sheath 12 in a relatively fixed position during movement of the needle assembly 14 between the retracted and extended positions 66 and 68.

The proximal end 62 of the control wire 58 is operably joined to the control handle 116, such as for example, to the integral thumb actuator 148 as shown or otherwise, for manipulation of the control wire 58. At least one aperture 122 is providing access for the control wire 58 to and from the access sheath 12 to the thumb actuator 148. The thumb actuator 148 is moved in either a clockwise or counterclockwise direction about the outer surface of the housing 118 to move the control wire 58 to bend the deflection section 42.

The main cannula 70 of the needle assembly 14 has a cannula hub 130 formed at the proximal end of the proximal portion 72. The proximal portion 72 extends proximally from the hub 120 of the access sheath 12. The housing 118 of the control handle 116 is disposed about the proximal portion 72 of the main cannula 70 and the cannula hub 130 extends proximally outward from the control handle 116. As illustrated, the proximal portion 72 includes grooves 132 that engage with grooves 134 of a threaded member 135, which is disposed about the main cannula 70, to position the main cannula 70 in a longitudinal position between the retracted and extended positions 66 and 68. For example, the threaded member 135 may be turned in a clockwise manner such that the grooves 134 of the threaded member 135 cooperatively engage the grooves 132 of the main cannula 70 to move the needle assembly 14 longitudinally to the extended position 68.

A syringe 140 is provided and is configured to interface with the cannula hub 130 for fluid communication with the central lumen 76. Preferably, when the main cannula 70 is in the extended position 68, the distal port 141 of the syringe 140 is positioned in the cannula hub 130 and the syringe 140 is actuated to advance therapeutic material into and through to the central lumen 76. The therapeutic material is then advanced through the needles 80 for delivery to the patient.

Referring to FIG. 4B, one other embodiment for the control handle 216 is provided. The control handle 216 has a housing 218 disposed about the sheath hub 120 to hold the proximal section 18 of the access sheath 12 in a relatively fixed position during movement of the needle assembly 14 between the retracted and extended positions 66 and 68. A thumb actuator 248 is operably connected to the proximal end 62 of the control wire 58 to bend the deflection section 42 when the thumb actuator 248 is moved along the housing 218 in a longitudinal direction either fore or aft to move the control wire 58 to bend the deflection section 42.

The control handle 216 includes at least one positive feature 250 that is formed and/or is molded into the housing 218. The positive feature 250 cooperatively engages at least one of a plurality of longitudinally spaced apart grooves 252 formed in the proximal portion 72 of the main cannula 70 to selectively hold the needle assembly 14 in a desired longitudinal position. For example, the main cannula 70 may be pushed or pulled, e.g., via the hub 130, to move the needle assembly 14 between the retracted and extended positions 66 and 68. When the needle assembly 14 reaches a desired position, the positive feature 250 engages one of the corresponding longitudinal grooves 252 to hold the needle assembly 14 in place. Other suitable control handle arrangements may also be employed with the present invention, such as for example, those disclosed in U.S. Patent Application Publication 2007/0203474 which is hereby incorporated herein by reference in its entirety.

Figure 5:
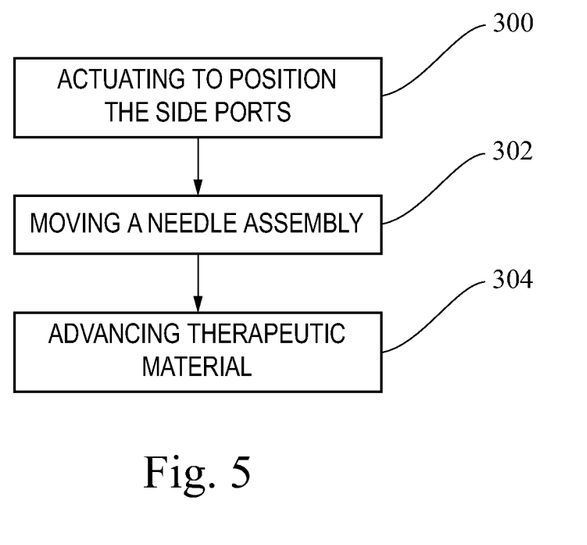
FIG. 5 is an example of a method for delivering therapeutic material to a patient in accordance with the present invention.

Referring to FIG. 5 is an example of one method for delivering a therapeutic material to a patient. The method comprises actuating a deflection section of the access sheath at 300 to bend at an angle to position a plurality of side ports formed in the distal section of the access sheath. A needle assembly is moved at 302 within the working lumen of the access sheath to an extended position to extend a plurality of needles through the side ports and outwardly from the access sheath. Therapeutic material is advanced at 304 through a central lumen of the main cannula of the needle assembly. The needles are in fluid communication with the central lumen to deliver the therapeutic material to the patient.

As a person skilled in the art will readily appreciate, the above description is meant as an illustration of the implementation of the principles of this invention. This description is not intended to limit the scope of the application for this invention and that the invention is susceptible for modification, variation and change, without departing from the spirit of this invention, as defined in the following claims.

I claim:

1. A medical device for delivering therapeutic material to a patient, the device comprising:
   an access sheath having a proximal section extending to a distal section and a working lumen formed in the proximal and distal sections, the distal section having a plurality of side ports formed therethrough in fluid communication with the working lumen, the distal section having a deflection section actuatable to bend at an angle for positioning the side ports in the patient; and
   a needle assembly configured to move within the working lumen between a retracted position and an extended position, the needle assembly including:
   a main cannula having a proximal portion extending to a distal portion comprising a distal wall, and a central lumen formed in the proximal and distal portions and terminating at the distal wall, the central lumen being configured to advance the therapeutic material; and
   a plurality of needles in fluid communication with the central lumen, the needles being attached to the distal portion of the main cannula proximal to the distal wall, the needles extending distally from the distal portion such that the needles are disposed within the access sheath in the retracted position and the needles extend through the side ports outwardly from the access sheath in the extended position to deliver the therapeutic material to the patient.

2. The medical device according to claim 1 wherein the central lumen has a diameter (d) and a flow area (A) defined by $(A)=(\pi(d)2)/4$ for advancing the therapeutic material to the needles.

3. The medical device according to claim 1 wherein the access sheath includes an elongated guide tip attached to the distal section and extending distal therefrom for guiding the access sheath in the patient.

4. The medical device according to claim 1 wherein the access sheath includes a coil disposed about the working lumen along the proximal and distal sections, the proximal section includes a first polymeric material and the deflection section includes a second polymeric material, the first and second polymeric materials respectively forming exteriors layers of the proximal and distal sections about the coil, the second polymeric material having a lower durometer than the first polymeric material.

5. The medical device according to claim 1 wherein the access sheath has at least one additional lumen and a control wire movably disposed in the additional lumen, the control wire having a first end connected to the distal section of the access sheath and a second end operably actuatable by an interventionalist for moving the control wire to bend the deflection section.

6. The medical device according to claim 1 wherein the side ports are formed through the deflection section at a radial interval of one of 90°, 120° and 180°.

7. The medical device according to claim 1 wherein the deflection section is spaced apart from and proximal to the side ports.

8. The medical device according to claim 1 wherein the side ports are each configured as a curved lumen for positioning the needles outwardly from access sheath when in the extended position.

9. The medical device according to claim 1 wherein each of the needles has a curved portion for positioning the needle outwardly from access sheath when in the extended position.

10. The medical device according to claim 1 wherein each of the needles has a distal metal section and a proximal plastic section that are joined together via an adhesive.

11. The medical device according to claim 1 wherein each of the needles has a distal metal section and a proximal plastic section that is overmolded about a portion of the distal metal section.

12. The medical device according to claim 1 wherein the needles are attached to the distal portion of the main cannula via one of soldering joints and welding joints.

13. A medical system for delivering therapeutic material to a patient, the system comprising:
   a control handle for actuation by an interventionalist;
   an access sheath operably connected to the control handle, the access sheath having a proximal section extending to a distal section and a working lumen formed in the proximal and distal sections, the distal section having a plurality of side ports formed therethrough in fluid communication with the working lumen, the distal section having a deflection section actuatable to bend at an angle for positioning the side ports in the patient in response to actuation of the control handle; and
   a needle assembly configured to move within the working lumen between a retracted position and an extended position, the needle assembly including:
   a main cannula having a proximal portion extending to a distal portion comprising a distal wall, and a central lumen formed in the proximal and distal portions and terminating at the distal wall, the central lumen being configured to advance the therapeutic material; and
   a plurality of needles in fluid communication with the central lumen, the needles being attached to the distal portion of the main cannula proximal to the distal wall, the needles extending distally from the distal portion such that the needles are disposed within the access sheath in the retracted position and the needles extend through the side ports outwardly from the access sheath in the extended position to deliver the therapeutic material to the patient.

14. The medical system according to claim 13 wherein the access sheath has at least one additional lumen and a control wire movably disposed in the additional lumen, the control wire having a first end connected to the distal section of the access sheath and a second end operably connected to the control handle for moving the control wire to bend the deflection section when the control handle is actuated.

15. The medical system according to claim 13 wherein the main cannula has a cannula hub formed at a proximal end of the proximal portion, the control handle disposed about the proximal portion of the main cannula and the cannula hub extending proximally outward from the control handle, the control handle including a threaded member that receives the cannula hub, the threaded member and the cannula hub each having grooves that cooperatively engage with each other to move the needle assembly between the retracted and extended positions.

16. The medical system according to claim 13 further comprising a syringe for containing the therapeutic material, the syringe configured to interface with the proximal portion of the main cannula to advance the therapeutic material into the central lumen.

17. The medical system according to claim 13 wherein the access sheath includes a coil disposed about the working lumen along the proximal and distal sections, the proximal section includes a first polymeric material and the deflection section includes a second polymeric material, the first and second polymeric materials respectively forming exteriors layers of the proximal and distal sections about the coil, the second polymeric material having a lower durometer than the first polymeric material.

* * * * *